(12) United States Patent
Teske

(10) Patent No.: US 8,536,468 B2
(45) Date of Patent: Sep. 17, 2013

(54) ELECTRICAL FEEDTHROUGH, IN PARTICULAR FOR MEDICAL IMPLANTS

(75) Inventor: Josef Teske, Hallstadt (DE)

(73) Assignee: BIOTRONIK SE & Co. KG, Berlin (DE)

( * ) Notice: Subject to any disclaimer, the term of this patent is extended or adjusted under 35 U.S.C. 154(b) by 287 days.

(21) Appl. No.: 13/043,886

(22) Filed: Mar. 9, 2011

(65) Prior Publication Data

US 2011/0232961 A1    Sep. 29, 2011

Related U.S. Application Data

(60) Provisional application No. 61/318,405, filed on Mar. 29, 2010.

(51) Int. Cl.
*H02G 3/08* (2006.01)

(52) U.S. Cl.
USPC ............... 174/650; 174/152 GM; 174/50.61; 361/302; 607/36

(58) Field of Classification Search
USPC .................. 174/152 GM, 50.61, 50.5, 50.55, 174/50.63, 650, 262, 520, 527, 152 G, 153 G; 361/302, 306.2, 328, 329, 306.1, 320, 321.1; 607/36, 37, 5; 439/935, 926, 587
See application file for complete search history.

(56) References Cited

U.S. PATENT DOCUMENTS

| | | | | |
|---|---|---|---|---|
| 5,751,539 A | * | 5/1998 | Stevenson et al. | 361/302 |
| 5,870,272 A | * | 2/1999 | Seifried et al. | 361/302 |
| 5,905,627 A | * | 5/1999 | Brendel et al. | 361/302 |
| 6,768,629 B1 | * | 7/2004 | Allen et al. | 361/302 |
| 6,888,715 B2 | * | 5/2005 | Stevenson et al. | 361/302 |
| 6,903,268 B2 | * | 6/2005 | Marshall et al. | 174/50.59 |
| 7,035,077 B2 | * | 4/2006 | Brendel | 361/302 |
| 8,200,328 B2 | * | 6/2012 | Stevenson et al. | 607/2 |
| 8,326,425 B2 | * | 12/2012 | Sprain et al. | 607/36 |

* cited by examiner

*Primary Examiner* — Angel R Estrada
(74) *Attorney, Agent, or Firm* — Buchanan Ingersoll & Rooney PC

(57) ABSTRACT

An electrical feedthrough, in particular for use in an electromedical implant, having a flange enclosing at least one feedthrough bushing and at least one terminal pin enclosed by the at least one feedthrough bushing, the terminal pin having at least one section which can be joined at a lower energy in the interior of the implant.

21 Claims, 7 Drawing Sheets

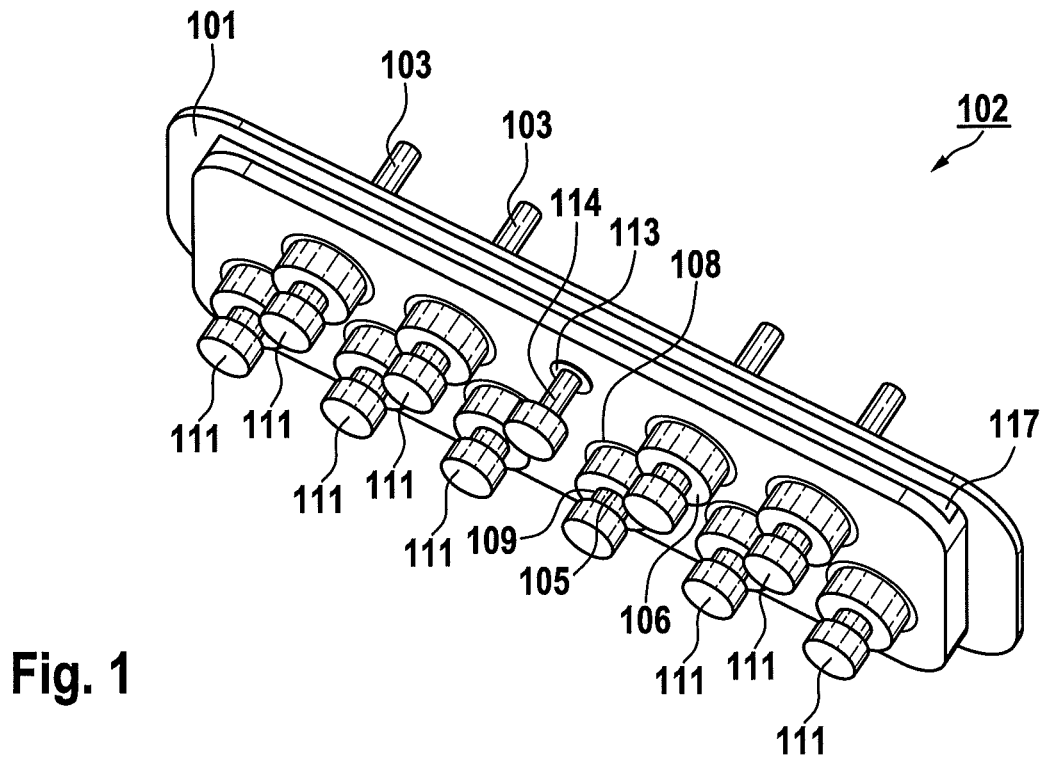
Fig. 1
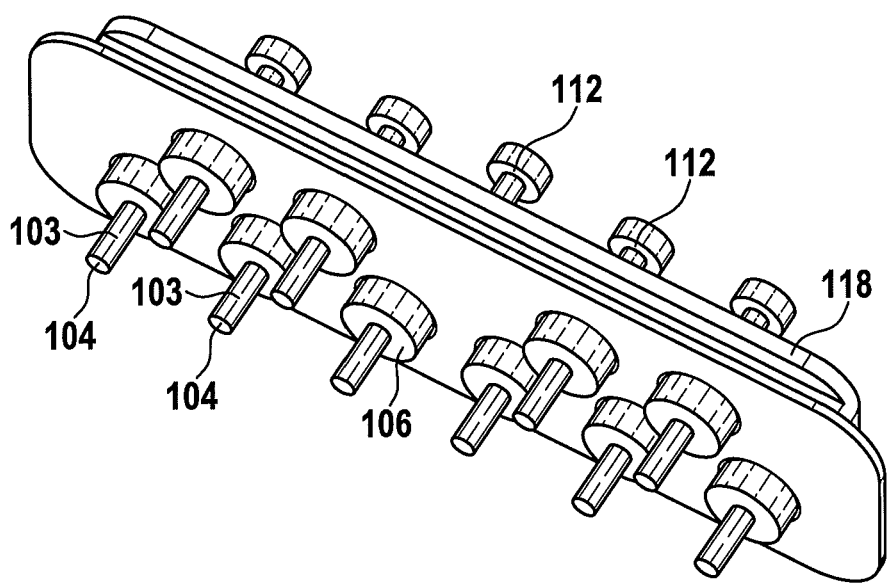

_(1)_

ELECTRICAL FEEDTHROUGH, IN PARTICULAR FOR MEDICAL IMPLANTS

RELATED APPLICATION

This patent application claims the benefit of U.S. Provisional Patent Application No. 61/318,405, filed on Mar. 29, 2010, which is hereby incorporated by reference in its entirety.

FIELD OF THE INVENTION

The present invention relates to an electrical feedthrough, suitable, in particular, for electromedical implants, such as, but not limited to, implantable cardiac pacemakers, defibrillators, cardioverters, nerve and cerebral stimulators, hearing aids, implantable medication pumps, and/or other electrically active implants, which include a hermetically sealed housing, and batteries having a hermetically sealed housing for these electronic implants.

BACKGROUND OF THE INVENTION

Such feedthroughs typically have a flange, through use of which they are inserted into a housing wall of the electromedical implant, preferably by a thermal joining method such as welding or soldering. An apparatus having, inter alia, a circuit board which is capable of processing or transmitting electrical signals, is located in the housing. The feedthrough has at least one feedthrough bushing, a flange enclosing the at least one feedthrough bushing, in which at least one terminal pin is seated, which is enclosed by the at least one feedthrough bushing. The terminal pin extends through the flange and the feedthrough bushing from an inner end in the interior of the housing to an outer end, which lies outside the hermetically sealed housing. The terminal pin is typically connected to the at least one feedthrough bushing and/or the at least one feedthrough bushing is typically connected to the flange using a soldered connection, preferably using a gold solder if metal coated feedthrough bushings are used, or using a bio-compatible glass solder (type 8625 from Schott) if uncoated feedthrough bushings are used. In consideration of the fact that the outer end of the terminal electrode can come into contact with the body tissue surrounding the implant in a medical implant, the terminal pins are typically manufactured from a biocompatible material, such as, but not limited to, niobium (Nb), platinum (Pt), iridium (Ir), platinum/iridium alloys (Pt/Ir), tantalum (Ta), titanium (Ti), zirconium (Zr), hafnium (Hf), medical stainless steel (e.g., 316L), or alloys made of these materials. FeNi, FeNiCo, FeCr, molybdenum (Mo), tungsten (W), chromium (Cr), FeCr, vanadium (V), aluminum (Al), or other alloys made of these materials are also possible as materials for the terminal pin. It will be apparent to one of ordinary skill in the art that other materials and alloys have similar properties may be utilized for the terminal pins without departing from the spirit and scope of the present invention.

The feedthrough bushing is typically produced from a ceramic material, such as aluminum oxide (Al2O3). Above all in the case of terminal pins made of niobium, tantalum, or titanium, the problem exists that only welding methods come into consideration in order to produce a connection to other conductors, for example, to the terminal lines or to device electronics attached to the circuit in the interior of the implant, for the production of secure, low-resistance, mechanically stable, and long-lived electrical contacts to the described biocompatible terminal pins. The required high temperatures of the welding procedure may generate metal vapors and/or welding sprays, however, which impair the electrical insulation capability of the ceramics and/or damage the circuit boards and therefore frequently require additional protective measures. Due to these properties, reflow soldering, which is well known in the electronics sector, has simple production technology, and is efficient, is also not possible or is not readily usable with such a terminal pin.

In the case of the described ceramic feedthroughs having platinum/iridium terminal pins, it is known that without special protective precautions, they display problems with the detachment of the metal coating of the feedthrough bushings upon the soldering using gold solder and have poor wettability of the platinum/iridium surfaces with soft solder. As a result, the noted reflow soldering is generally unreliable.

Fundamentally, the coating of the pin surfaces in the case of niobium, tantalum, or titanium terminal pins on the inner side for easy wettability with soft solder for the attachment to the internal electronics is either not possible at all or is only possible with increased effort, in that metal coatings which can be soft soldered are applied using welding technology or plasma-physical pathways, for example. Surfaces or coatings which can be soft soldered on nickel, tantalum, or titanium, which are applied with the aid of fluxes or using electroplating, have been unknown up to this point.

A feedthrough for implantable medical devices having an integrated capacitive filter is known from U.S. Pat. No. 5,870,272, in which the electrical contacting and mechanical connection between a pin comprising niobium, for example, and an inner contact circuit with the capacitive filter interposed is produced via a complex, multistep soldering configuration using hard and soft solders. This design is too complex for feedthroughs having simple terminal electrodes, and efficient manufacturing would not be possible in the case of a corresponding layout of the feedthrough.

The present invention is directed toward overcoming one or more of the above-identified problems.

SUMMARY OF THE INVENTION

The present invention is based on the object of disclosing a hermetically sealed feedthrough for terminal electrodes made of a body-compatible material toward the implant outer side, which is contact-connectible in a manner having simple production on their inner end to the electronics situated there, in particular using reflow soldering.

This object is achieved in that the terminal pin has a bio-compatible section and, in the interior of the implant, a section which can be joined at a lower energy, and preferably can be soft soldered. The inner end of the terminal pin and/or the intersection can additionally be implemented in the form of a nailhead.

The section of the terminal pin which can be joined at a lower energy and can preferably be soft soldered provides the advantage that the terminal pin can be joined in the interior of the implant securely and easily using lower energy—for example, lower heat energy up to 450° C., which is used above all in soft soldering processes. In particular, in a reflow process, cost-effective soft soldering can be produced simultaneously with other components on the electronic circuit board of the implant. These sections of the terminal pins may be installed together with the other components of the electrical feedthrough in the form of the at least one feedthrough bushing simultaneously in a common high-temperature soldering process, which in turn represents a particularly cost-effective mode of attachment. Furthermore, the formation of brittle phases between the section of the terminal pin and the soft solder used is avoided by use of the section of the terminal pin which can be joined at a lower energy in the interior of the implant, as otherwise formed, for example, between gold electrodes and soft solders having tin components.

Optionally, the sections of the terminal pin which can be joined at a lower energy may additionally also be provided with coatings which can be soft soldered particularly well, i.e., are easily wettable, having materials such as palladium (Pd), silver (Ag), copper (Cu), gold (Au), and alloys made of these materials, the coating having a layer thickness up to approximately 0.5 mm and a thickness up to approximately 200 μm in the case of a gold coating. A gold coating having this layer thickness is known not to form brittle phases together with soft soldering materials containing tin components.

In summary, because of the design according to the present invention of the electrical feedthrough, only biocompatible surfaces are offered toward the implant outer side and only electrode areas which can be soft soldered are offered toward the interior. The latter are capable, for example, of being processed further in a reflow soldering method for the contacting. Materials for the biocompatible section of the terminal pin are, for example, Nb, Ta, Ti, Pt, Pt/Ir, Zr, Hf, medical stainless steels such as 316L, or alloys of these materials, as well as FeNi, FeNiCo, FeCr, Mo, W, Cr, V, Al, or alloys made of these materials. Materials for the section which can be joined at lower energy are nickel, copper, palladium, gold, silver, iron, or alloys made of these materials. These alloys may also contain one or more of the following elements in addition to the listed elements: zinc (Zn), tin (Sn), cadmium (Cd), lead (Pb), antimony (Sb), arsenic (As), bismuth (Bi), phosphorus (P), silicon (Si), nitrogen (N), or beryllium (Be). One of ordinary skill in the art will appreciate that other materials and alloys have similar properties may be utilized or other implemented without departing from the spirit and scope of the present invention.

The section made of the above listed materials, or other similar materials, which can be joined at a lower energy can be an attachment which is located on the inner end of the terminal pin. This attachment can be implemented as a pin, on the one hand, which is advantageously located in an extension of the longitudinal axis of the terminal pin and allows the ready accommodation of further components such as filters to ensure the electromagnetic compatibility (EMC filters) in the form of capacitors because of the lack of thickened areas. Alternatively, the attachment can also be implemented as a disk or round blank, which offers larger areas to the corresponding contact points on the partner circuit board as an advantage during the reflow process and allows mechanically stronger connections having higher carrying capacities.

The attachment which can be joined at a lower energy is preferably attached using a joint to the biocompatible section of the terminal pin, in particular hard solder alloys containing, for example, copper (Cu), silver (Ag), copper-nickel (CuNi), copper-zinc (CuZn), copper-tin (CuSn), silver-copper (AgCu), silver-copper-zinc (AgCuZn), silver-copper-zinc-tin (AgCuZnSn), silver-copper-tin (AgCuSn), silver-copper-zinc-cadmium (AgCuZnCd), copper-phosphorus (CuP), copper-phosphorus-silver (CuPAg), or copper-gold (CuAu), using which temperature inhomogeneities during the brazing process may be compensated for. Brazing using gold solder/gold solder alloys is preferred. Further, alloys thereof having additional possible alloy additives such as Pb, Sb, As, Bi, P, N, Be, Ni are also possible. Furthermore, the attachment which can be joined at a lower energy can be soldered, welded, crimped, clamped, or glued in an electrically conductive manner on the biocompatible section of the terminal pin using a joint, but is preferably brazed using gold solder. Preferably, the joint between the biocompatible section and the attachment which can be joined at a lower energy is located inside the implant housing in relation to the connection solder. This is the preferred type of attachment, because it is simple, reliable because of a lack of brittle phases, has mechanical carrying capacity, and can be implemented simultaneously together with the further feedthrough components in the same soldering process of the feedthrough. Because this attachment occurs already before the attachment to the electrical circuit in the interior of the implant, a welding or brazing procedure can be performed therein at the joint. In a preferred embodiment, the joint can be located within the at least one feedthrough bushing. It may thus be implemented easily in the soldering process of the feedthrough because of the centering action of the feedthrough bushing and may additionally protect it from mechanical strains and further influences. Furthermore, it is particularly preferably possible to also enclose it in the glass solder. This results in more extensive protection from mechanical strains, because the joint and the adjoining pin areas are mechanically decoupled toward the exterior by the glass solder.

In a further preferred embodiment, the electrical feedthrough includes an outer and an inner feedthrough bushing. In this embodiment, the at least one terminal pin is connected hermetically sealed to the outer and the inner feedthrough bushings and the outer and inner feedthrough bushings are connected hermetically sealed to the flange using a soldered connection implemented as a glass plug. The glass plug is delimited by a cavity which is enclosed by the flange, and the outer and the inner feedthrough bushings. The glass solder of the type 8625 from Schott, which was cited at the beginning, is preferably used as the solder material. However, other solder materials are also contemplated. The feedthrough bushings are thus used as flow barriers during the soldering, which results in a simplification and a yield increase of the production process. In further embodiments, either the outer or the inner feedthrough bushings, or also both, may be dispensed with, if suitable materials or material combinations are selected for the flange, the terminal pins, and the glass solder for this purpose. These variants have the advantage that the soldering can be performed in a more space-saving manner than with two feedthrough bushings simultaneously.

The security against incident radiation in the housing and thus the prevention of the introduction of radiation is very important due to modern imaging methods and also because of the radiation present in the environment, for example, due to mobile telephones, wireless networks, magnetic resonance tomographs, and the like. For this reason, the electrical feedthrough can comprise a filter, preferably a filter capacitor, which is electrically connected to the section which can be joined at a lower energy, preferably to the pin which can be soft soldered. A shield between the flange and the at least one terminal pin is produced by the filter and the circuit lying inside the housing and the further components are thus protected against electromagnetic incident radiation. The suitable filters are typically ceramics, which are generally very sensitive to heat and fracture. Therefore, these may only be attached directly without further complex measures using a low-energy method, such as a soft soldering method.

Furthermore, the present invention includes a production method for an electrical feedthrough, in which the terminal pin is cooled using a heat sink during the generation of the glass solder plug. Because the terminal pin remains cooler than the glass in this case, even upon the use of terminal pin materials having coefficients of thermal expansion which are otherwise incompatible with the glass solder, the occurring thermal strains may be controlled enough that hermetically sealed soldering having mechanical carrying capacity is achieved. The heat introduction into the glass solder can be performed by IR radiation (for example, of a CO2 lasers) or inductive heat coupling via the surrounding flange, inter alia.

Furthermore, the present invention includes the use of the feedthrough according to the present invention, with soft soldering on the terminal pin being executed using a reflow method. In addition, exterior soft soldering can be executed using a reflow method simultaneously with the interior soft soldering.

Preferred refinements of the terminal electrode feedthrough are disclosed, whose features, details, and advantages will become clear from the following description of the exemplary embodiment on the basis of the appended drawing.

DESCRIPTION OF THE DRAWINGS

FIG. 1 shows a spatial illustration of a feedthrough according to the present invention having ten terminal pins for implant signals and having an eleventh terminal pin for the electrical ground connection.

DETAILED DESCRIPTION

Figure 2:
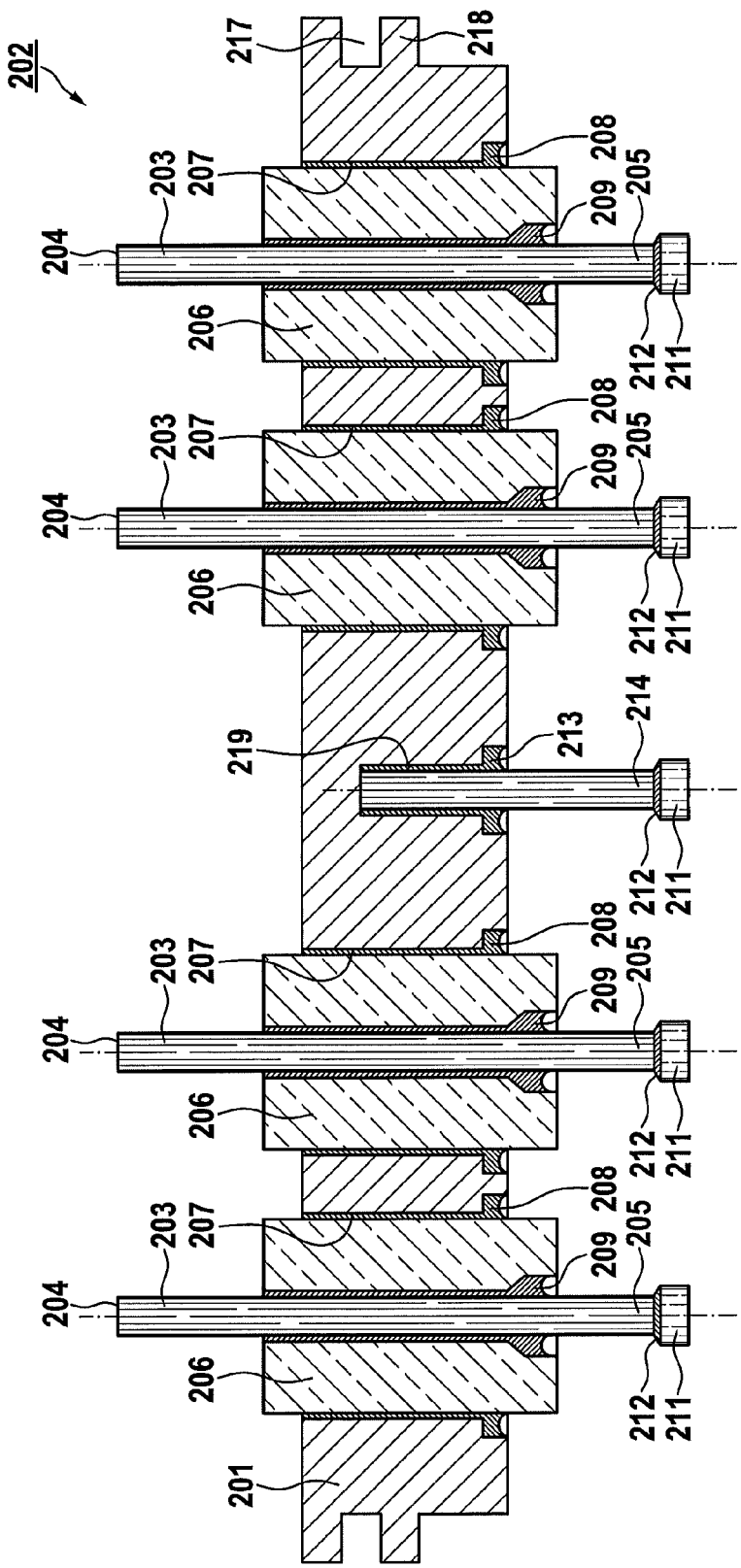
FIG. 2 shows a sectional illustration of a further embodiment of the feedthrough according to the present invention.

FIG. 1 generally shows an electrical feedthrough in a spatial illustration of a fundamental construction of a series feedthrough 102 having a view of the inner side (protruding into the implant interior) and the outer side. The electrical feedthrough includes a flange 101, which preferably consists of, but is not limited to, Ti, Nb, Ta, Zr, alloys made of one or more of the elements, or further additive elements such as, but not limited to, Hf, Al, Fe, P, Si, Mn, or C, or ceramic, in which multiple feedthrough bushings 106 are located, to which terminal pins 103 are connected by soldered connections. An attachment 111, which can be soft soldered, of the terminal pin 103 in the form of a disk can be recognized on the inner view, which is electrically and mechanically attached to the terminal pin 103 by a joint 112. The components identified therein are described further in FIG. 2. The feedthrough is constructed in this and the following figures as a series feedthrough having a series made of ten feedthrough bushings 106 and terminal pins 103 and series having four or six such feedthrough bushings and terminal pins. A ground pin 114, which also has an attachment 11 which can be soft soldered, is located in the latter. However, any number of feedthrough bushings and terminal pins may be implemented without departing from the spirit and scope of the present invention.

FIG. 2 shows the section of a further embodiment of the electrical feedthrough 202. Identical or similar components are identified using reference numerals based on FIG. 1, but in the two-hundred series of numbers, and are not explained once again here. For example, the reference numeral 102 in FIG. 1 identifies the same component as the reference numeral 202 in FIG. 2.

The flange 201 preferably guides at least one cylindrical feedthrough bushing 206 made, for example, of biocompatible Al2O3 in its flange openings 207. Each of the bushings is soldered using a soldered connection 208 made, for example, of biocompatible, metal hard solder to the flange 201. The feedthrough bushings 206 are provided in this embodiment with a metal coating in the area of the flange openings 207, preferably a biocompatible coating made of niobium, in order to make them wettable by the hard solder and thus allow soldering. In the variant shown here, the ceramic feedthrough bushings 206 protrude beyond the flange 201 on both sides and ensure sufficiently long electrical insulation sections for high-voltage applications of the feedthrough 202.

The terminal pin 203 preferably has a simple cylindrical shape, an outer end 204 and an inner end 205, and is connected using a soldered connection 209 to the feedthrough bushing 206 and is thus fixed together with the feedthrough bushing in the flange 201. Both of the soldered connections 208 and 209 are implemented in the production phase as soldered rings, which are located between the flange 201 and the feedthrough bushings 206 and/or between feedthrough bushings 206 and terminal pins 203. These rings are liquefied by heating, for example, via electrical resistance heating, electrical induction, heat conduction, or infrared radiation, and form a biocompatible, mechanically stable, hermetically sealed soldered connection which can be loaded with alternating temperatures after cooling.

An attachment 211 which can be soft soldered, preferably in the form of nickel discs, is attached via a joint 212 on the inner end 205. To be able to produce the listed soldered connections 208, 209, and joints 212 cost-effectively in the same process, the materials of the soldered connections and the joint preferably include the same soldering material, such as, for example, gold solders, gold-niobium, gold-tantalum, gold-titanium, or gold-zirconium alloys. Alternatively, for example, copper, silver, copper-nickel, copper-zinc, copper-tin, silver-copper, silver-copper-zinc, silver-copper-zinc-tin, silver-copper-tin, silver-copper-zinc-cadmium, copper-phosphorous, copper-phosphorous-silver, or copper-gold alloys or numerous further alloys may be used in order to compensate for temperature inhomogeneities during the brazing process. These joints lying on the implant interior do not have to be implemented as biocompatible like the terminal pins lying on the implant interior, because they are separated from the outer side by the hermetically sealed implant housing and the hermetically sealed feedthrough.

As the preferred material combination, niobium is selected for the terminal pin 203 or 214, nickel for the attachment 211 which can be soft soldered, and refined gold for the hard solder 212 or 215, because refined gold generates soldered connections with both niobium and also with nickel which are miscible with one another in any alloy ratio and always form ductile phases. The resulting brazed connections are sufficiently stable that upon mechanical strain, the terminal pins 203 or 214 tear or fail in most cases, and not the brazed connections 212.

Alternatively, however, it is also advantageous for processing technology to join the joint 212 between terminal pin 203 and attachment 211 using a hard solder having a higher melting point or to weld them directly without an additive in a first method step, in order to subsequently solder them in a second brazing process to the other components of the feedthrough 202, so that possible problems—for example, in the case of complex and/or more spacious structures—with undesired temperature inhomogeneities are avoided. It is essential that soft solder having a tin component is not used in the joint 212, in order to avoid brittle phases, which have little mechanical carrying capacity, between gold and tin.

Furthermore, the electrical feedthrough according to the embodiment shown includes a ground pin 214, for which the observations just made with respect to the soldered connections also apply.

The inner surfaces of the attachments 211 of the terminal pins 203 and the ground pin 214 are preferably all approximately located in a common plane and thus allow successful reflow soldering, but may also intentionally lie in different planes, if this is required by the adaptation to the corresponding substrate of the implant.

In the embodiment shown here, the flange 201 has a groove 217 for receiving the half shells of an implant housing (not shown). A lip 218 is simultaneously used as a welding protection during the laser welding of the flange 201 to the housing half shells of the implant.

Figure 3:
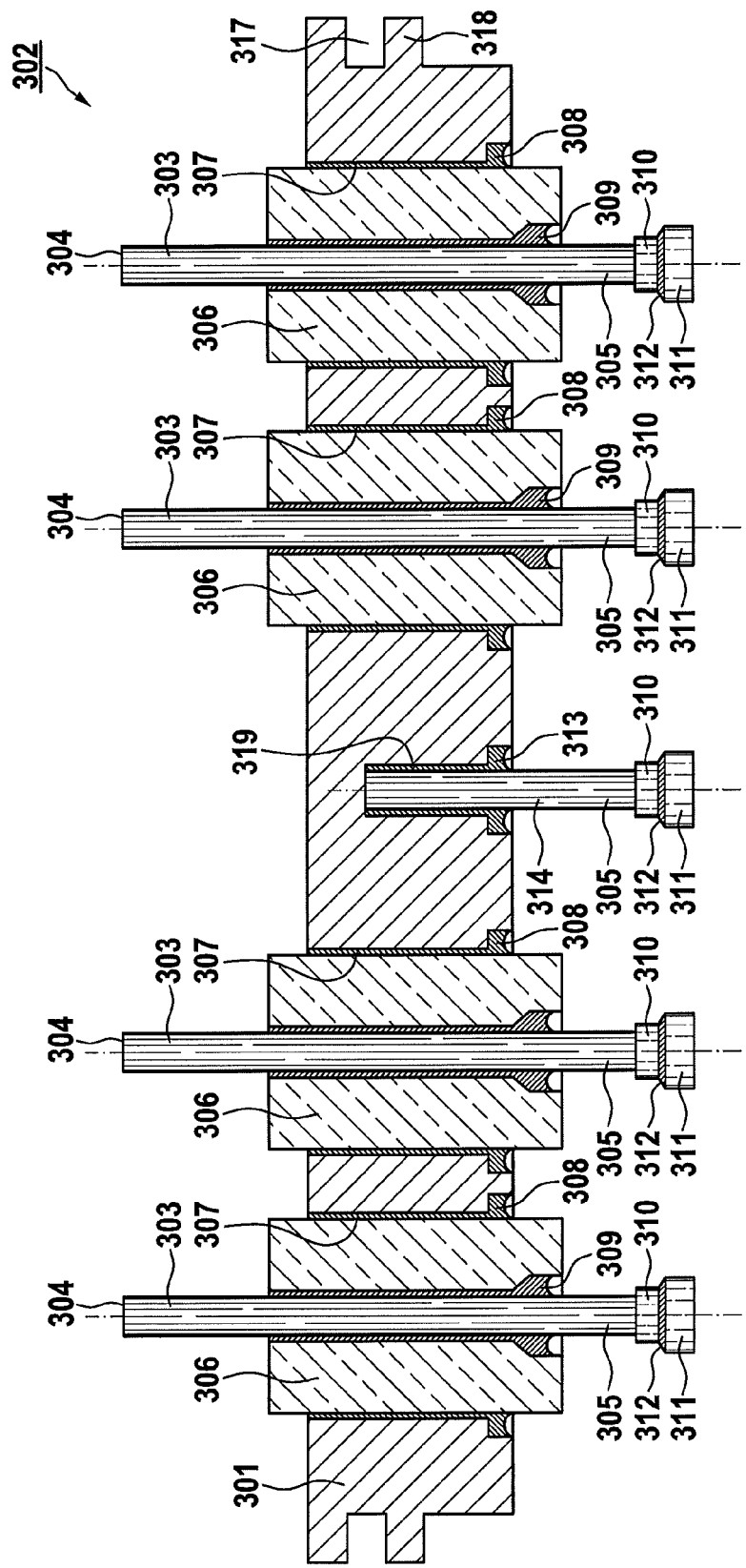
FIG. 3 shows a sectional illustration of a variant of the feedthrough according to the present invention from FIG. 2 having four nailhead-shaped terminal pins for implant signals and one nailhead-shaped ground pin.

FIG. 3 shows a further variant of the embodiments from FIG. 1 and FIG. 2. As before, identical or similar components are identified using reference numerals based on FIG. 2, but in the three-hundred series of numbers, and are not explained once again here. The pins 303 have nailhead-like or plate-like attachments (also called "nailheads") 310 on the inner end 305. Better orientation of the attachments 311 which can be soft soldered is thus made easier and more precise common planarity is achieved.

Figure 4:
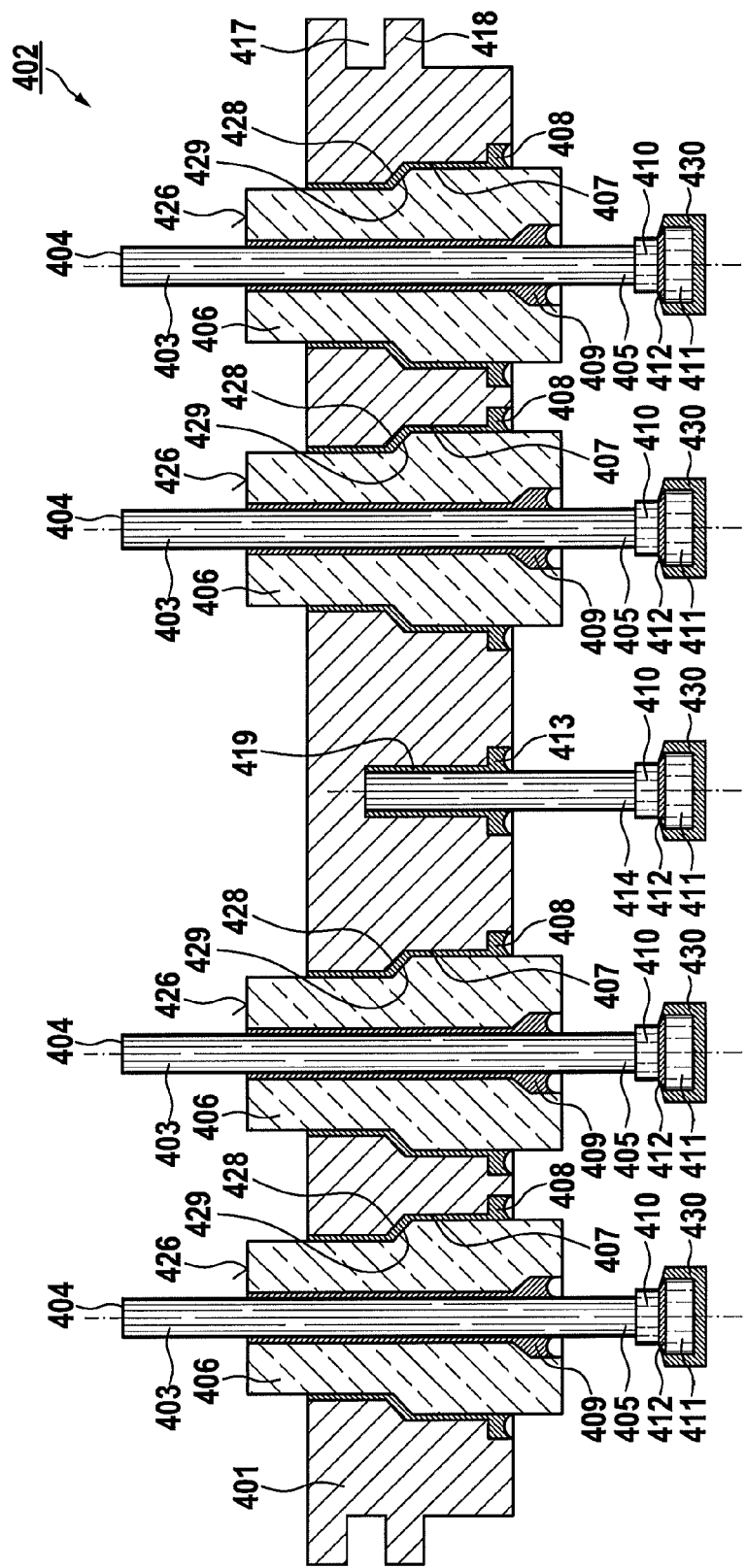
FIG. 4 shows a sectional illustration of a further variant of the feedthrough according to the present invention having five terminal pins, which are provided with a coating (pre-tinning) which improves the reflow soft soldering.

FIG. 4 shows a further or additional variant to the previously described embodiments. Identical or similar components are identified using reference numerals based on the previously described figures, but in the four-hundred series of numbers, and are not explained once again here. Before the actual reflow process, the attachments 411, which can be soft soldered on the terminal pins 403 and the ground pins 414, are wetted at least on their front face with a coating or layer 430, preferably made of soft solder Sn37Pb, for example, from Weidinger or Zevaton, with suitable fluxes being used as aids for good wetting of the front faces of the attachments 411, preferably of the standardized type "Alpha 850-33". However, other fluxes such as aqueous solutions or solutions containing hydrochloric acid which are made of zinc chloride/ammonium chloride, alcohol-based solutions with dimethyl amine hydrochloride, or aqueous solutions made of strong activated halogenides are also suitable. All of these fluxes offer the advantage that after the completed wetting of the attachments 411 with soft solder 430, they can be removed again from the feedthrough in a simple cleaning method using aqueous solutions without residues and possible leakage paths in the feedthrough are not concealed by flux residues, so that the feedthroughs may be tested reliably for hermeticity using helium leak tests.

The soft soldering surface is additionally brought into a common plane by a separate method—for example, by thermal pretreatment or by grinding. In general, a better common flatness is achieved using the layers 430 made of soft solder than is possible using the attachments 411 alone, so that production-related irregularities of the attachments 411 which can be soft soldered are compensated for using the layer. Furthermore, the coating provides favorable conditions for a reflow soft soldering method, because it is no longer necessary to first achieve the most complete possible wetting of the attachments 411 with soft solder during the reflow soldering, because the surfaces of the attachments 411 are already nearly completely wetted with soft solder. The lateral surfaces of the disc-shaped attachments 411 may also be wetted by the soft solder layer 430. Even if the joints 412 containing gold solder are also unintentionally wetted using soft solder containing tin, and Au—Sn brittle phases are formed in the transition zones, the Au—Sn brittle phases do not represent a disadvantage in this configuration, because the Au—Sn brittle phases do not assume a mechanical function, are not noticeably mechanically loaded, and have ductile coherence with the remainder of the soft solder layer 430, so that no components or particles of the soft solder 430 detach in the further application of the feedthrough. The inner ends 405 of the terminal pin 403 or the ground pin 414 may also be nailhead-shaped, as shown in FIG. 3.

It is advantageous for the method technology if both the feedthrough bushings 406 and also the inner walls of the openings 407 of the flange 401 have corresponding bevels or steps 428 and 429. A tapered bushing outer surface 426 is thus formed, which generally protrudes further out of the flange 401 than without tapering, in order to ensure a sufficient installation section. Using this configuration, the ceramic can be centered in the inner cavity of the flange before the preparation of the soldered connection 408 and does not have to be held in position by additional aids.

Figure 5:
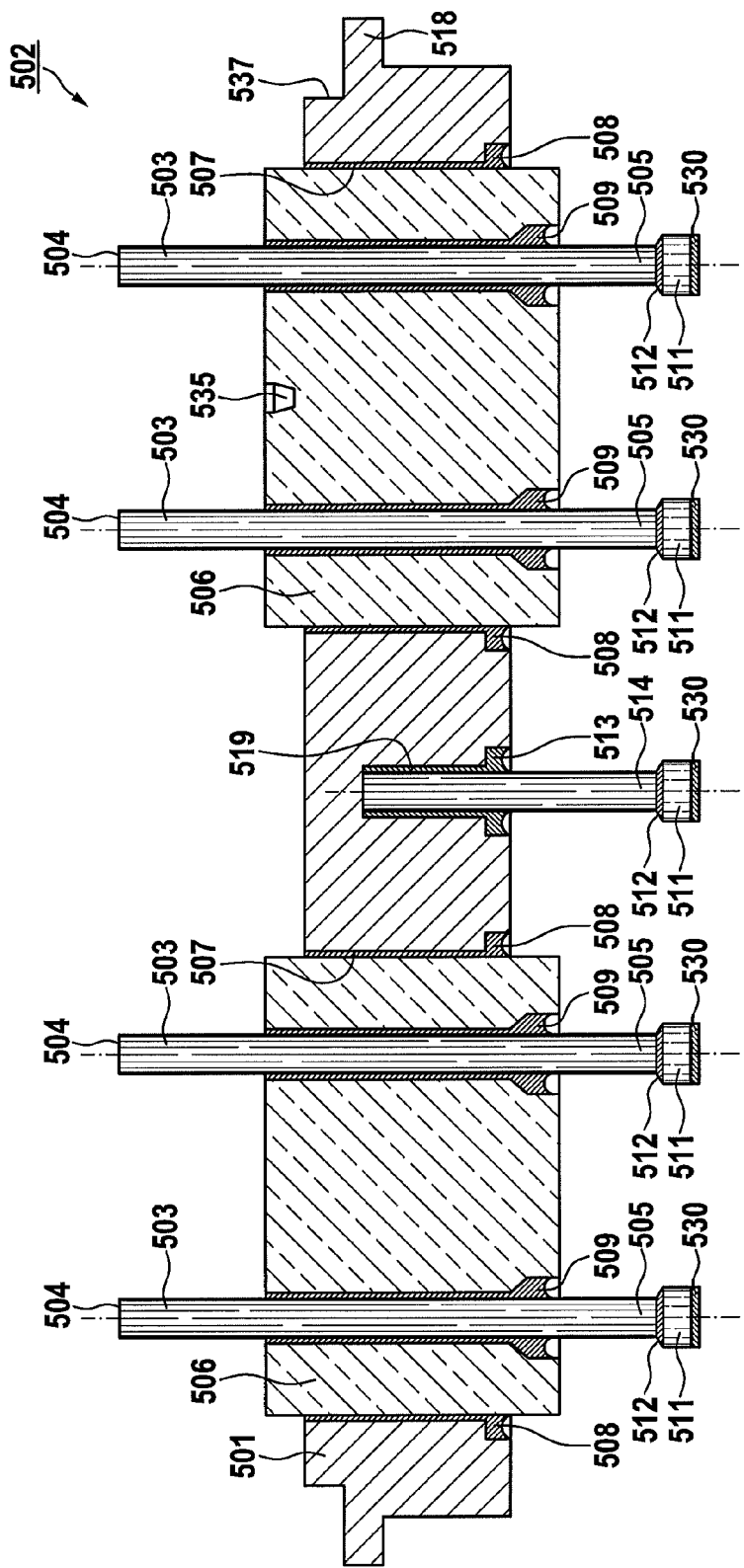
FIG. 5 shows a sectional illustration of the additional variants of the feedthrough according to the present invention from FIG. 2 having five terminal pins, one feedthrough bushing leading at least two terminal electrodes and the terminal pins being provided with a coating which improves the soft soldering capability.

FIG. 5 shows a further variant compatible with the prior embodiments, in which two or more pins 503 are soldered into a common ceramic 506. Identical or similar components are identified using reference numerals based on the previously described figures, but in the five-hundred series of numbers, and are not explained once again here. The common ceramics 506 may have depressions or so-called "slots" 535, which lengthen the electrical insulation sections between the pins 503 among one another and/or the pins 503 and the flange 501, and thus increase the high-voltage stability of the feedthrough. In this embodiment, the attachments 511, which can be soft soldered are provided with a coating 530 which can be soft soldered particularly well, for example, made of palladium, silver, gold, copper, or alloys of these materials. Gold coatings having thicknesses of up to approximately 200 µm are particularly preferred, because they do not form brittle phases with the tin of the soft solder at these layer thicknesses. The coated attachments 511 are preferably stamped out of nickel plates or films which are coated on both sides and are therefore preferably only provided on one front face with coatings 530 which can be soft soldered particularly well for the subsequent reflow process. The coating 530 and the other coating pointing toward the pin, at which the joint 512 is located, may include different materials and have different thicknesses, the other coating pointing toward the pin being particularly suitable for the hard soldering with the terminal pins 503 and the ground pin 514, and the other coating 530 being particularly suitable for the reflow soft soldering. The attachments 511 may also additionally have coatings on their lateral surfaces which can be soft soldered particularly well, which ensures improved mechanical carrying capacity of the soft solder connections produced during the reflow soft soldering in this case.

In this variant, the flange 501 has a fitting 537, which is used for welding into an opening of the implant housing (not shown). A stop or a lip 518 is simultaneously used as a welding protection during the laser welding of the flange 501 to the housing or the housing half shells of the implant.

Figure 6:
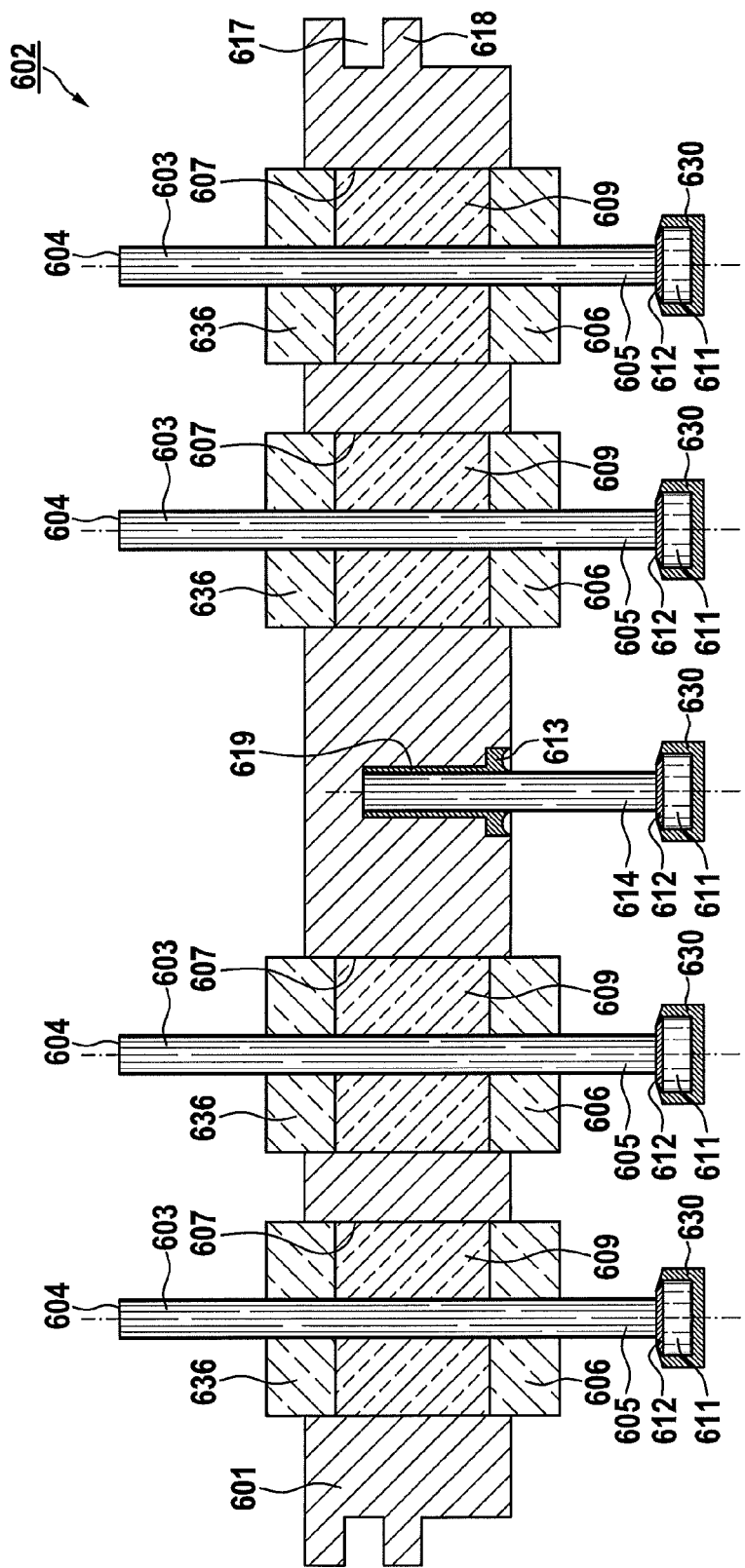
FIG. 6 shows a sectional illustration of an alternative embodiment of the feedthrough according to the present invention having five terminal electrodes and having components soldered using glass.

A special embodiment is shown in FIG. 6. Identical or similar components are identified using reference numerals based on the previously described figures, but in the six-hundred series of numbers, and are not explained once again here. An inner feedthrough bushing 606 and an outer feedthrough bushing 636 are attached in each inner opening 607 of the flange 601, which form a cavity with the flange 601. The terminal pins 603 are soldered using a preferably biocompatible glass solder 609 to the flange 601 and the feedthrough bushings 606 and 636, the glass solder also being located in the cavity and completely or nearly completely filling it. The feedthrough bushings 606 and 636 form a flow barrier for the glass solder 609 during the soldering, i.e., they prevent the glass solder 609 from flowing away out of the opening 607 of the flange 601 during the soldering process. Upon selection of the correct glass solder 609, preferably glass solder of the type 8625 from Schott, the ground pin 614 can be soldered using hard solder 613 in the opening 619 of the flange 601, and also the attachments 611 can be soldered using the joint 612, because glass solder generally allows a wide temperature range of the processing, in the same soldering and/or heating process. In the case of a glass/ceramic feedthrough, the soldered connection 609 preferably includes a biocompatible glass solder, which simultaneously wets the flange 601, the terminal pins 603, and the feedthrough bushings 606 and 636 and whose coefficient of thermal expansion is preferably adapted to the wetted components.

In further variants, the feedthrough bushings 606 and/or 636 may optionally be left out simultaneously, if suitable materials or material combinations are selected for the flange, the terminal pins, and the glass solder for this purpose. In such cases, for example, the glass solder is adjusted in its composition so it is less oxidizing or even reducing, so that the metal surfaces are less attractive to the glass solder, the surface tension of the glass solder dominates in the brazing, and finally the glass does not flow out of the openings 607 during the processing in spite of low viscosity. These variants have the advantage that the soldered connections may be executed in a more space-saving manner overall than using two feedthrough bushings simultaneously. In further variants, the openings 607 may have bevels or steps, which form a positioning aid for the glass solder in the openings 607.

Figure 7:
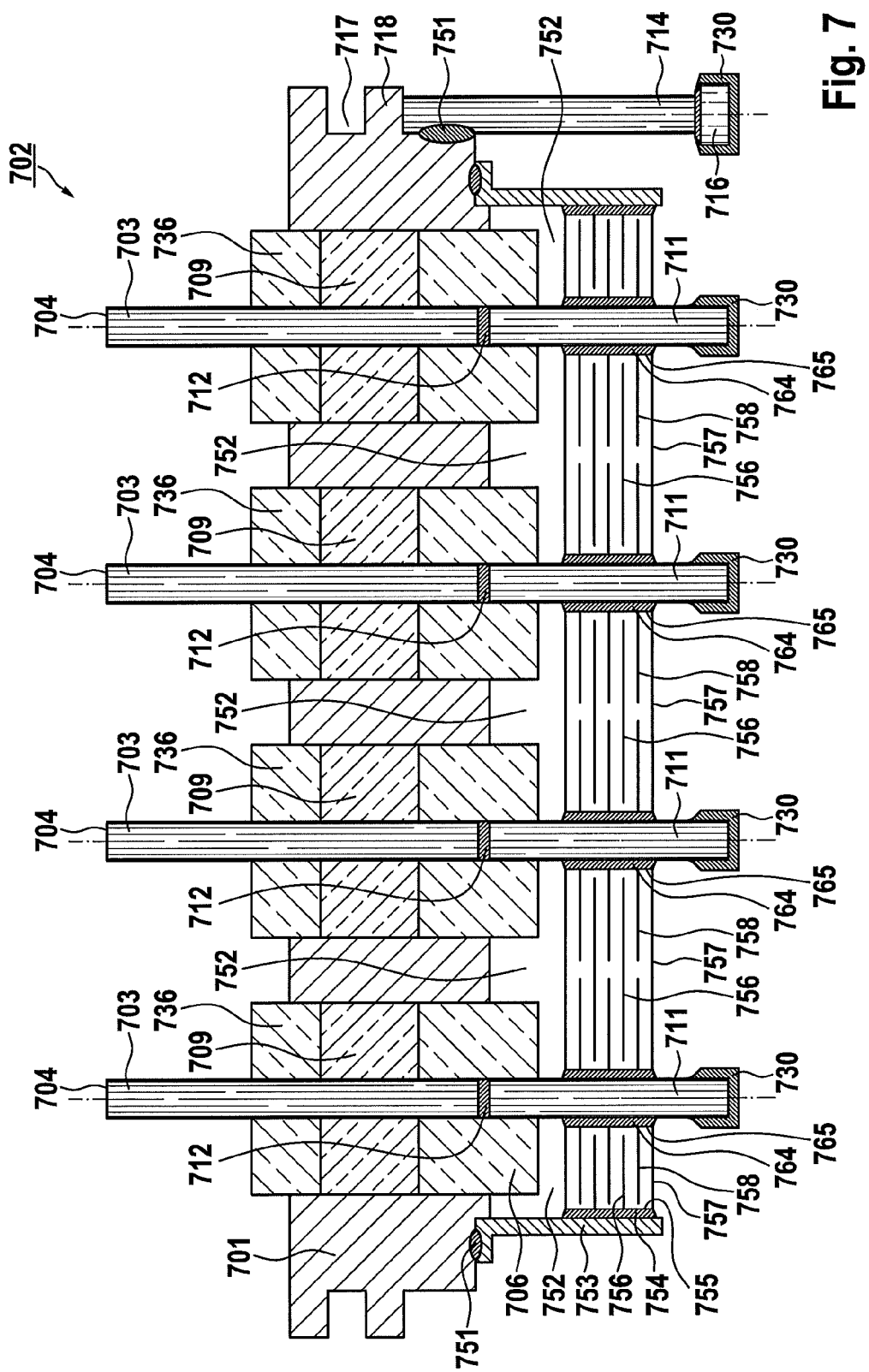
FIG. 7 shows a sectional illustration of a further embodiment of the feedthrough according to the present invention having a filter capacitor.

FIG. 7 shows a further embodiment of the invention. Identical or similar components are identified using reference numerals based on the previously described figures, but in the seven-hundred series of numbers, and are not explained once again here. A filtered feedthrough 702 having a flange 701 is shown in FIG. 7, which has an inner feedthrough bushing 706, an outer feedthrough bushing 736, and a glass solder plug 709 lying between them. A terminal pin, which is implemented in two parts and fixed by the glass solder plug 709, is shown in each of these feedthrough bushings 706 and 736. It includes an outer biocompatible section 703, on which a pin 711, which can be soft soldered, is attached at a joint 712. The solder material of the joint 712 can be one of the abovementioned solder materials. The joint 712 can have been fixed during the production method by the glass solder plug so that it is located inside the inner feedthrough bushing 706, in order to thus be protected against mechanical and chemical influences. Furthermore, the electrical feedthrough comprises a ground pin 714, which is electrically and mechanically connected in this embodiment variant to the flange 701 using a spot weld 751. The ground pin 714 can include the same biocompatible material as the biocompatible section 703 of the terminal pin, or also the same material in which the flange 701 includes, which can improve the welding capability, but includes a section 716 which can be soft soldered in the form of a disc. Both the pins 711 which can be soft soldered and also the section 714 of the ground pin which can be soft soldered may be provided with a soft solder coating 730 for better attachment and form a nearly common plane ("common zone") for the reflow process by a special thermal method or by grinding.

For electromagnetic filtering, in this variant a filter capacitor 757 is used, which is held on the flange using a bushing 753. The bushing 753 is electrically and mechanically attached on the flange 701 using one or more spot welds or weld seams 751, with the flange 701 being able to have a depression for better positioning of the bushing 753 in relation to the flange 701. The spot welds 751 are applied so that a leak test connection is provided between the bushing 753 and the flange 701.

The filter capacitor 757 includes laminar electrodes 756 and 758, which are embedded in a dielectric material 757, which includes barium titanate, for example. The electrodes 756 have a metal plating 755 which can be soft soldered on the outer side of the capacitor, made of palladium, silver, copper, or their alloys, for example. An electrical and mechanical ground connection is performed on this metal plating via a fixed soldered connection 754 to the bushing 753 fastened on the flange 701. The electrodes 758 are also provided with a metal plating 765 which can be soft soldered, also made of palladium, silver, copper, or their alloys, at the openings of the capacitor, through which the pins 711, which can be soft soldered, extend and using which the soldered connection 764 is soldered to the pins 711 which can be soft soldered, in order to form the electrical connections to the electrical signals of the electrical implant. For reasons of better manufacturing, the soldered connections 764 and 754 may include various soft solders having different melting points or ranges. A material composition is preferably selected as the material for the soldered connection 754, for example, PbSn3.5Ag1.5, which has a higher processing temperature at a soldering range of 305° C. than the material of the soldered connection 764 having the preferred material composition of, for example, PbSn5Ag2.5 and a soldering temperature of 280° C. Thus, in a preferred production method, the capacitor 757 can first be soldered onto the bushing 753, which can be soft soldered using the higher-melting-point soft solder 754, the bushing 753 having the soldered-on capacitor 757 can be pushed over the pins 711 and electrically and mechanically attached on the flange 701 using welds 750, then finally can be soldered onto the pins 711 which can be soft soldered using a lower-melting-point soft solder 764, without the higher-melting-point soft solder 754 running the danger of melting again during the second soft soldering using the soft solder 764 and detaching from the metal plating 755 and losing the electrical/mechanical connection to the capacitor electrodes 756. The electrical feedthrough thus produced can be tested for hermeticity between the inner and outer sides of the implant using a helium leak test, because the leak test connection provides a passage to the cavity 752, which is delimited by the flange 701, bushing 753, capacitor 757, and the individual inner feedthrough bushings 706 and pins 711 which can be soft soldered, through which the helium can flow.

In further variants of this embodiment, instead of a single capacitor 757, multiple independent capacitors may also be used. It is also possible to only filter individual terminal pins using capacitors 757 (for example, for an antenna attachment for wireless transmission of signals out of the implant). The electrical and mechanical attachment of the capacitor 757 can also be implemented using electrically conductive adhesives, using, for example, welding, clamps, or plugs, special value always being placed on the leak test capability of the configuration. The leak test capability can alternatively or additionally be implemented by additional openings (not shown) in the capacitor 757, in the solders 754 and 764, and/or in the bushing 753. The flange 701 can alternatively be shaped so that instead of the bushing 753, the flange continues at a similar point and receives the capacitor 757 and has an additional opening for the leak test capability in the wall thus resulting (not shown here) to the cavity 752.

In all of the described embodiments, joining technologies and forms other than those listed may also be used, for example, by welding, clamping, electrically conductive gluing, bonding, and the like.

In further variants, the pins 711 may also be attached to the flange 701 and filtered using the examples offered in FIGS. 2-5.

In further reasonable variants, all combinations and geometric modifications from FIGS. 1-7 may be implemented and are part of this patent application.

It will be apparent to those skilled in the art that numerous modifications and variations of the described examples and embodiments are possible in light of the above teachings of the disclosure. The disclosed examples and embodiments are presented for purposes of illustration only. Therefore, it is the intent to cover all such modifications and alternate embodiments as may come within the true scope of this invention, which is to be given the full breadth thereof. Additionally, the disclosure of a range of values is a disclosure of every numerical value within that range.

| List of reference numerals: | |
|---|---|
| 101, 201, 301, 401, 501, 601, 701 | flange |
| 102, 202, 302, 402, 502, 602, 702 | feedthrough |
| 103, 203, 303, 403, 503, 603, 703 | terminal pin |
| 104, 204, 304, 404, 504, 604, 704 | outer, biocompatible end of the terminal pin |
| 105, 205, 305, 405, 505, 605, 705 | inner end of the terminal pin |
| 106, 206, 306, 406, 506, 606, 706 | feedthrough bushing, inner feedthrough bushing |
| 207, 307, 407, 507, 607, 707 | opening in the flange |
| 108, 208, 308, 408, 508, 607, 708 | soldered connection between flange and feedthrough bushing |
| 109, 209, 309, 409, 509, 609, 709 | soldered connection between terminal electrode and feedthrough bushing |
| 310, 410 | nailhead-like attachment on the inner end of the terminal pin |
| 111, 211, 311, 411, 511, 611, 711 | attachment of the terminal pin which can be soft soldered |
| 112, 212, 312, 412, 512, 612, 712 | joint between terminal pin and attachment |
| 113, 213, 313, 413, 513, 613, 713 | soldered connection between ground pin and flange |
| 114, 214, 314, 414, 514, 614, 714 | ground terminal pin or ground pin |
| 117, 217, 317, 417, 517, 617, 717 | groove in the flange for receiving the implant housing halves |
| 118, 218, 318, 418, 518, 618, 718 | interior lip |
| 219, 319, 419, 519, 619 | opening to receive the ground pin |
| 428 | step in the flange |
| 429 | step in the feedthrough bushing |
| 430, 530, 630, 730 | soft solder (flattened on the end) or coating which can be soft soldered or layer which can be soft soldered on the attachment |
| 535 | "slot" or depression in the feedthrough bushing 506 to enlarge the insulation section, e.g., between two pins 503 or between one pin 503 and the flange 501 |
| 636, 736 | outer feedthrough bushing |
| 537 | weld fitting in the flange |
| 751 | spot welds or weld seams 750 |
| 752 | cavity |
| 753 | metal bushing which can be soft soldered and welded |
| 754 | soldered connection between bushing 753 and metal plating 755 of the capacitor 757 |
| 755, 765 | metal plating of the capacitor 757 |
| 756, 758 | capacitor electrode |
| 757 | ceramic dielectric material |
| 764 | soldered connection between pin 711 which can be soft soldered and metal plating 765 of the capacitor 757 |

I claim:

1. An electrical feedthrough for use in an electro-medical implant comprising:
at least one feedthrough bushing, wherein the at least one feedthrough bushing comprises:
an inner feedthrough bushing disposed at an interior of the implant; and
an outer feedthrough bushing disposed at an exterior of the implant;
a flange which encloses the at least one feedthrough bushing; and
at least one terminal pin, which is enclosed by the at least one feedthrough bushing, wherein the terminal pin has a biocompatible section and a section which can be joined at a low energy in the interior of the implant,
wherein the at least one terminal pin is connected via a hermetically sealed connection to the outer and inner feedthrough bushings, and the outer and inner feedthrough bushings are connected via a hermetically sealed connection to the flange, both hermetically sealed connections using a soldered connection implemented as a glass solder plug, the glass solder plug being delimited by a cavity enclosed by the flange and the outer and inner feedthrough bushings.

2. The electrical feedthrough according to claim 1, wherein an inner end of the terminal pin is implemented as nailhead-shaped.

3. The electrical feedthrough according to claim 1, wherein the biocompatible section of the terminal pin comprises Nb, Ta, Ti, Pt, Ir, Zr, Hf, medical stainless steels, Pt/Ir, and/or alloys made of these materials, and/or FeNi, FeNiCo, FeCr, Mo, W, Cr, FeCr, V, Al, and/or alloys with these materials.

4. The electrical feedthrough according to claim 1, wherein the section of the terminal pin which can be joined at a low energy comprises an attachment, which is located on an inner end of the terminal pin.

5. The electrical feedthrough according to claim 4, wherein the attachment comprises nickel, copper, palladium, gold, silver, iron, and/or alloys made of these materials.

6. The electrical feedthrough according to claim 4, wherein the attachment which can be joined at a low energy in the interior of the implant is implemented as a pin.

7. The electrical feedthrough according to claim 6, further comprising a filter capacitor electrically and mechanically connected to the pin which can be joined at a low energy, wherein the filter capacitor produces a shield between the flange and the at least one terminal pin.

8. The electrical feedthrough according to claim 4, wherein the attachment which can be joined at a low energy in the interior of the implant is implemented as a disk.

9. The electrical feedthrough according to claim 4, wherein the attachment which can be joined at low energy in the interior of the implant is joined using soft soldering.

10. The electrical feedthrough according to claim 9, wherein an interior soft soldering on the at least one terminal pin is executed using a reflow method.

11. The electrical feedthrough according to claim 4, wherein the attachment which can be joined at a low energy is attached using a joint biocompatible section of the terminal pin.

12. The electrical feedthrough according to claim 11, wherein the attachment which can be joined at a low energy is attached using the joint biocompatible section of the terminal pin via brazing, welding, crimping, clamping, or gluing on in an electrically conductive manner.

13. The electrical feedthrough according to claim 11, wherein the attachment which can be joined at a low energy is attached using the joint biocompatible section of the terminal pin via brazing using gold solder.

14. The electrical feedthrough according to claim 11, wherein the joint is located inside the at least one feedthrough bushing.

15. The electrical feedthrough according to claim 1, wherein the at least one feedthrough bushing comprises ceramic material.

16. The electrical feedthrough according to claim 15, wherein the ceramic material comprises aluminum oxide (Al2O3).

17. The electrical feedthrough according to claim 1, wherein the at least one terminal pin is connected via a hermetically sealed connection to the at least one feedthrough bushing, and/or the at least one feedthrough bushing is connected via a hermetically sealed connection to the flange.

18. The electrical feedthrough according to claim 17, wherein the hermetically sealed connections comprise soldered connections.

19. The electrical feedthrough according to claim 18, wherein the soldered connections use a glass solder.

20. A method for producing an electrical feedthrough according to claim 1, comprising the step of cooling the at least one terminal pin using a heat sink during the generation of the glass solder plug.

21. The electrical feedthrough according to claim 1, wherein the biocompatible section of the at least one terminal pin and the section of the terminal pin which can be joined at a low energy are connected together at a joint located inside the inner feedthrough bushing.

* * * * *